US012693285B2

(12) United States Patent
Stevanato et al.

(10) Patent No.: US 12,693,285 B2
(45) Date of Patent: Jul. 28, 2026

(54) DEVICE AND METHOD FOR MEASURING THE WATER CONTENT OF THE GROUND, VEGETATION AND/OR SNOW

(71) Applicant: FINAPP S.R.L., Montegrotto Terme (IT)

(72) Inventors: Luca Stevanato, Montegrotto Terme (IT); Marcello Lunardon, Montegrotto Terme (IT); Sandra Moretto, Montegrotto Terme (IT)

(73) Assignee: FINAPP S.R.L., Padua (IT)

( * ) Notice: Subject to any disclaimer, the term of this patent is extended or adjusted under 35 U.S.C. 154(b) by 244 days.

(21) Appl. No.: 18/263,317

(22) PCT Filed: Feb. 11, 2022

(86) PCT No.: PCT/IB2022/051238
§ 371 (c)(1),
(2) Date: Jul. 27, 2023

(87) PCT Pub. No.: WO2022/175793
PCT Pub. Date: Aug. 25, 2022

(65) Prior Publication Data
US 2024/0085397 A1      Mar. 14, 2024

(30) Foreign Application Priority Data
Feb. 18, 2021      (IT) ........................ 102021000003728

(51) Int. Cl.
*G01N 33/24* (2006.01)
*G01T 3/06* (2006.01)

(52) U.S. Cl.
CPC ............. *G01N 33/246* (2013.01); *G01T 3/06* (2013.01)

(58) Field of Classification Search
CPC ................................ G01N 33/246; G01T 3/06
(Continued)

(56) References Cited

U.S. PATENT DOCUMENTS

2011/0204243 A1* 8/2011 Bendahan ............... H01J 40/04
250/367
2012/0175525 A1* 7/2012 Frank ........................ G01T 7/00
250/336.1
(Continued)

FOREIGN PATENT DOCUMENTS

CN            2039422 U   *  6/1989
WO      WO-2020141406 A1 *  7/2020  ............... G01T 3/06

OTHER PUBLICATIONS

International Search Report and Written Opinion received for PCT Serial No. PCT/IB2022/051238 on May 9, 2022, 12 pgs.
(Continued)

*Primary Examiner* — Marrit Eyassu
(74) *Attorney, Agent, or Firm* — Merchant & Gould P.C.

(57) ABSTRACT

A device for measuring water content of the ground, vegetation and snow includes an ambient neutron detector to measure ambient neutron flow, having first and second sheets made at least partially with a scintillator. A light meter measures light conveyed by a light guide interposed between the first and second sheets. The ambient neutron detector transforms interaction with particle(s) into an electric charge. A programmable control unit connects to the ambient neutron detector, and includes an integrating circuit transforming the electric charge produced by interaction with the particle(s) into a signal. The control unit processes the signal to discriminate a signal generated by ambient neutron, incident cosmic rays and/or background noise, and measures ambient neutron flow, incident cosmic rays, and/or background noise. The measurement of the water content is obtained from measurement of normalized ambient neutron flow with respect to measurement of cosmic rays flow incident to the ground.

11 Claims, 5 Drawing Sheets

(58) Field of Classification Search

USPC ............................................................. 73/73

See application file for complete search history.

(56) References Cited

U.S. PATENT DOCUMENTS

| 2013/0181137 | A1* | 7/2013 | Watanabe | ............... | C30B 29/12 |
| | | | | | 250/369 |
| 2017/0090049 | A1* | 3/2017 | Ramsden | ................. | G01T 3/06 |

OTHER PUBLICATIONS

Stevanato Luca, et al., "A Novel Cosmic-Ray Neutron Sensor for Soil Moisture Estimation over Large Areas", Agriculture, vol. 9, No. 9, Sep. 14, 2019 (Sep. 14, 2019), p. 202, XP055849946, ISSN: 2077-0472, DOI: 10.3390/agriculture9090202, p. 3, paragraph 3-p. 4, paragraph 1, p. 6, paragraph 6, figures 1 and 2.

Weimar, Jannis, et al., "Large-Scalre Boron-Lined Neutron Detection Systems as a 3He Alternative for Cosmic Ray Neutron Sensing", Frontiers in Water, vol. 2, Sep. 17, 2020 (Sep. 17, 2020), XP055825789, DOI: 10.3389/frwa.2020.00016, figure 2.

Cester D., et al., "A Novel Detector Assembly for Detecting Thermal Neutrons, Fast Neutrons and Gamma Rays", Nuclear Instruments & Methods in Physics Reasearch. Section A, Elsevier BV* North-Holland, NL, vol. 830, May 24, 2016 (May 24, 2016), pp. 191-196, XP029652597, ISSN: 0168-9002, DOI: 10.1016/J. NIMA.2016.05.079. The Whole Document.

Egner, Bryan V., et al., "Characterization of a Boron-Loaded Deuterated Liquid Scintillator for Fast and Thermal Neutron Detection", Nuclear Instruments & Method in Physics Research. Section A, vol. 996, Feb. 16, 2021 (Feb. 16, 2021), p. 165153, XP055849977, NL. ISSN: 0168-9002, DOI: 10.1016/j.nima.2021.165153. The Whole Document.

Italian Search Report received for Italian Serial No. 202100003728 on Oct. 15, 2021, 3 pgs.

* cited by examiner

DEVICE AND METHOD FOR MEASURING THE WATER CONTENT OF THE GROUND, VEGETATION AND/OR SNOW

CROSS-REFERENCE TO RELATED APPLICATIONS

The present application is a National Stage Filing of PCT International Application No. PCT/IB2022/051238 filed on Feb. 11, 2022, which claims priority to Italian Patent Application No. 102021000003728, filed on Feb. 18, 2021, which is incorporated in its entirety herein by reference.

FIELD OF APPLICATION

The present invention relates to a device and a method for measuring the water content of the ground, vegetation and snow. In particular, the present invention relates to a device and a method for measuring the water content of the ground, vegetation and snow on a large scale.

PRIOR ART

As is known, measurements of the water content may be carried out using different types of devices.

For example, it is known to measure the water content of the ground by exploiting point probes of the electromagnetic type, from which it is possible to obtain an indication relating to a volume of ground of about one cubic decimeter (dm³).

There are also systems that exploit remote sensing and use images from satellites or drones. Through mathematical models, the information collected is then correlated with that available from weather stations or other centers that provide databases relating to climatology.

There are also some attempts to apply a technology based on the measurement of environmental neutrons induced by cosmic rays on the ground. Indeed, it has been shown that there is a correlation between the ambient neutron flow and the average water content of ground, vegetation and snow.

As known, the production of energy neutrons between the epithermal and the slow (0.5 eV-50 keV) is regularly influenced by the presence of hydrogen, which in turn is directly linked to the water content. This information, suitably processed by mathematical models, is suitable for responding to the need to know in real time (from hourly to daily) the condition of water availability of cultivated land, of snow and vegetation. Furthermore, this measurement provides averaged information over an area extended up to a few hectares, and up to depths of about 50-60 cm.

In the international patent application WO 2020/141406 A1 a device for measuring the water content of the ground, vegetation and/or snow is described.

The device comprises a module adapted to measure a cosmic ray flow incident on the ground and a second module adapted to measure an ambient neutron flow.

In this device, the measurement of the incident cosmic ray flow is used to correct the measurement of the ambient neutron flow. In fact, as is well known, the ambient neutron flow, in addition to the humidity of the ground, also depends on the incident cosmic ray flow, which in turn depends on the geographical position, the time of year and the local atmospheric conditions. The technical solution proposed by WO 2020/141406 A1 represents an undoubted advantage over the previous prior art which used cosmic ray flow values provided by research centers.

While this solution represents undoubted progress compared to previously known systems, it is not without drawbacks.

Firstly, the device has two independent detection modules inside, which must be designed to coexist in a compact environment.

Furthermore, both modules must be calibrated both for the information collected and for each other, to ensure that the measurements may be compared and used to measure the water content.

DISCLOSURE OF THE INVENTION

The need is therefore felt to solve the drawbacks of the Prior Art.

The need is felt to have a more compact device compared to the devices of the prior art.

The need is felt to have a device for measuring the water content which is easier to manage than known devices.

Furthermore, the need is felt to provide a device for measuring the water content which is less expensive than the devices of the prior art, but which at the same time allows even more reliable information to be obtained than the systems of the prior art.

Furthermore, the need is felt to simplify the control circuit in order to reduce the possibility of breakage of the pieces and further reduce energy consumption.

These requirements are met, at least partially, by a device for measuring the water content of the ground, vegetation and/or snow, and by a method for measuring the water content of the ground, vegetation and/or the snow.

DESCRIPTION OF THE DRAWINGS

Further features and advantages of the present invention will become more apparent from the following description of preferred and non-limiting embodiments thereof, in which.

Elements or parts of elements common to the embodiments described hereinafter will be indicated with the same reference numerals.

DETAILED DESCRIPTION

Figure 1:
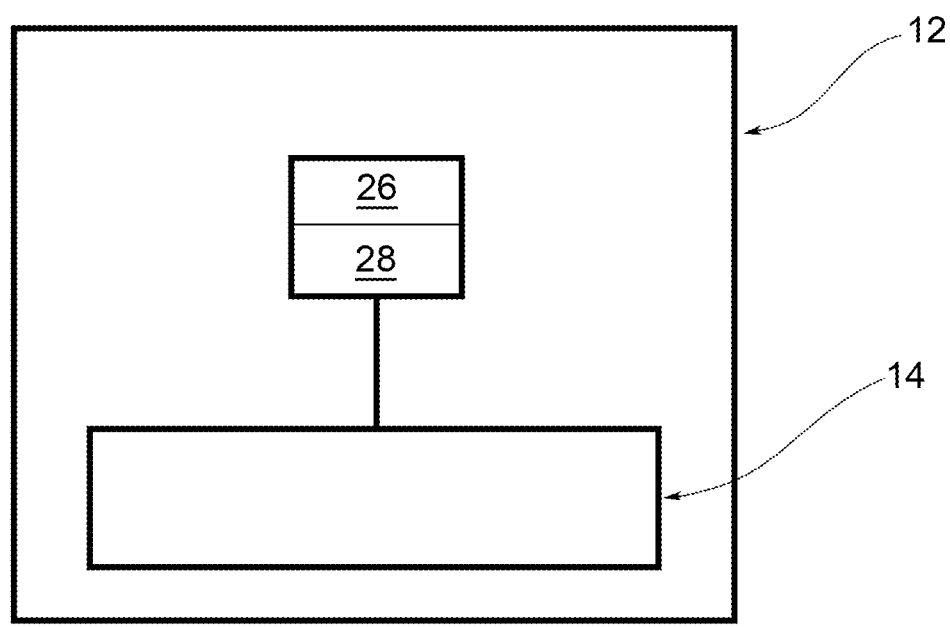
FIG. 1 schematically shows a device for measuring the water content according to an embodiment of the present invention.
Figure 2:
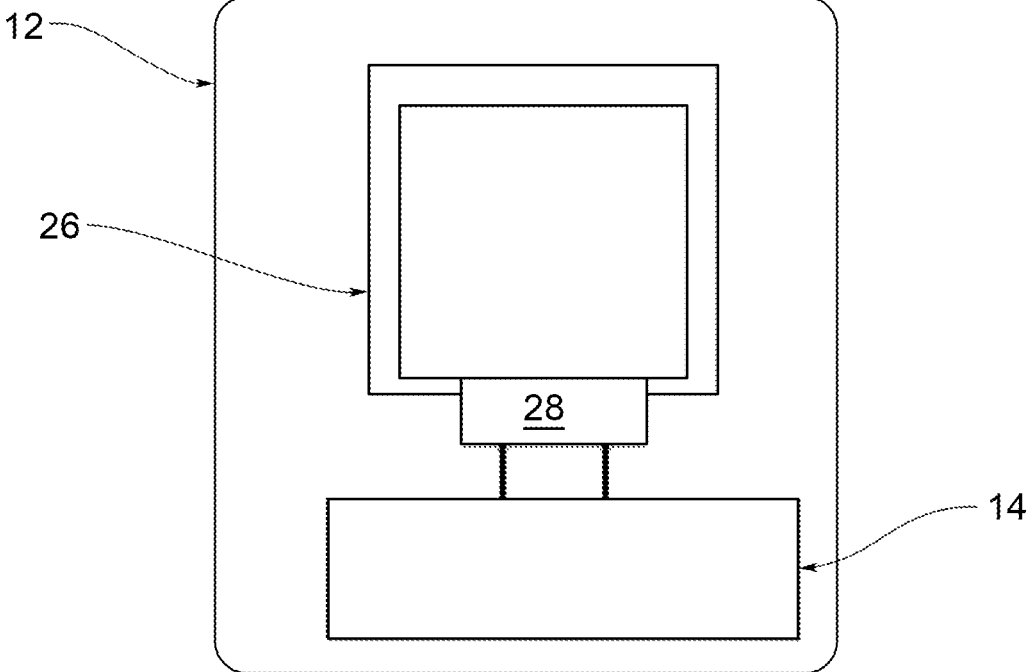
FIG. 2 schematically shows an alternative embodiment of a device for measuring the water content of the ground according to the present invention.
Figure 3:
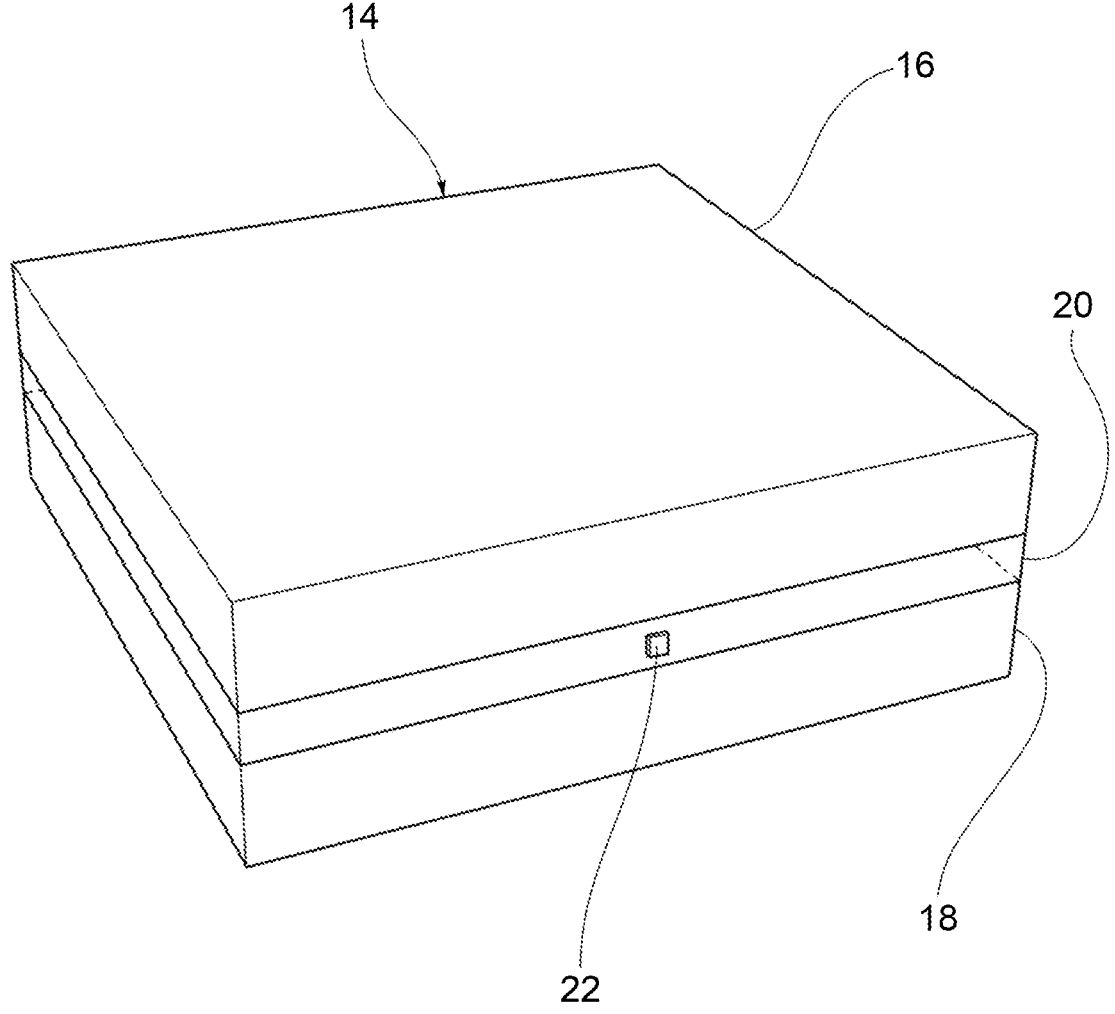
FIG. 3 schematically shows a component of a device according to an embodiment of the present invention.

FIG. 1 schematically shows as a whole a device for measuring the water content of the ground, vegetation and/or snow, which is indicated by the reference numeral 12.

The device 12 for measuring the water content of the ground, vegetation and/or snow comprises at least one ambient neutron detector 14 adapted to measure an ambient neutron flow.

The ambient neutron detector is of the type comprising at least a first sheet 16 and a second sheet 18 made at least partially with a scintillator, wherein a light guide 20 is interposed between the first sheet 16 and the second sheet 18.

The ambient neutron detector 14 further comprises at least one light meter 22, 24 adapted to measure the light conveyed by the light guide 20, and is adapted to transform the interaction with at least one particle into an electric charge.

The device 12 further comprises a control unit 26, of the programmable type, and operatively connected to the at least one ambient neutron detector 14.

The control unit 26 comprises an integrating charge circuit 28 in which the electric charge produced by the interaction with the at least one particle is transformed in a signal.

Moreover, the control unit 26 is adapted to process the signal so as to discriminate a signal generated by ambient neutron, incident cosmic rays and/or background noise, and obtaining a measurement of ambient neutron flow, incident cosmic rays, and/or background noise.

The measurement of the water content of the ground, vegetation and/or snow is therefore obtained from the measurement of the normalized ambient neutron flow with respect to the measurement of the cosmic rays flow incident to the ground. According to a possible embodiment, the control unit 26 may be suitable for the calculation of at least three parameters of the following type:

a first parameter is the time necessary for the signal to reach a predetermined fraction of its maximum value;
a second parameter is the maximum value of the signal;
a third parameter is the ratio between the partial charge in a time interval having a predetermined length and the total integrated charge.

In other words, the at least one light meter 22, 24 produces an electric current signal $i(t)$ when it detects a particle. Depending on the type of particle interacting with the at least one light meter 22, 24, the signal has a duration which may range from a few fractions of μs to about 10 μs.

The integrating circuit 28 integrates the electric current signal $i(t)$ over time obtaining a voltage signal $s(t)$, which depends on the time interval considered.

Therefore the second parameter, i.e. the maximum value of the signal $s(t)$, represents the total integrated charge, considered in the time interval from 0 to maximum time when the signal $s(t)$ stops growing as a result of a current signal $i(t)$ equal to zero. The temporal development of the signal depends on the type of particle that has interacted with the at least one light meter 22, 24. For times shorter than the maximum time, the signal will have a value corresponding to a part of the integrated total charge, i.e. a partial charge in a time interval of predetermined length.

Through the use of the type of parameters mentioned above, it is possible to identify the shape of a signal, regardless of its amplitude by:

obtaining a signal normalized to one through the third parameter;
evaluating the time taken by the signal to reach a predetermined value, or by evaluating the value of a signal reached after a predetermined time.

Through the use of these parameters, the signals are distinguishable from each other on the basis of correlations between the types of parameters mentioned above.

Figure 8:
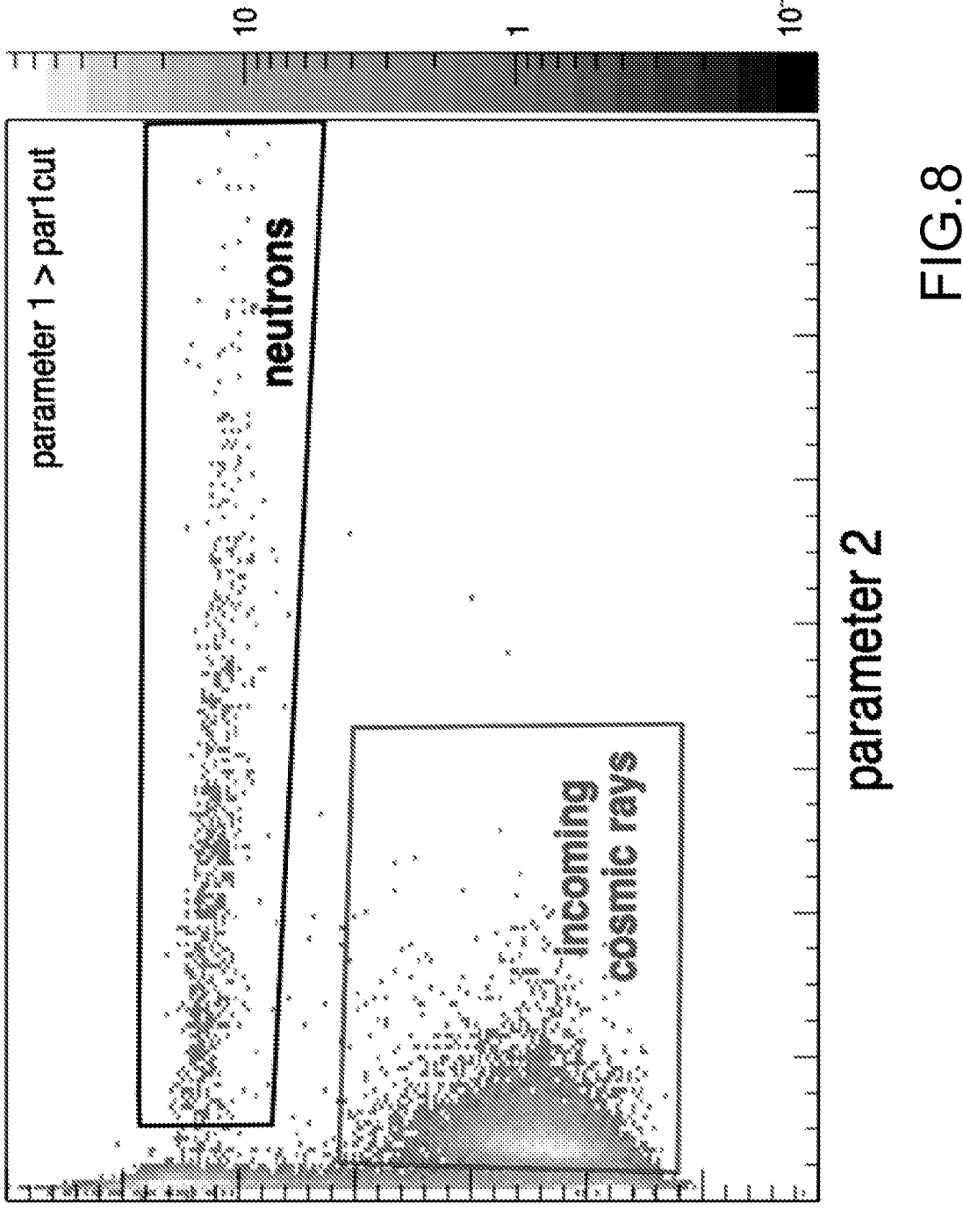
FIG. 8 shows a possible embodiment of a correlation graph between parameters calculated by means of a device according to the present invention.

In this regard, FIG. 8 schematizes the use of the parameters just mentioned. The figure represents in a Cartesian plane the correlation between the second parameter and the third parameter, after a first preselection on the first parameter within an interval in which the signal is more probable.

Advantageously, the first parameter may be considered within a window comprised between a first minimum parameter and a first maximum parameter.

Similarly, as regards the second parameter, it may be considered with a condition in which the second parameter is greater than a second minimum parameter.

Through the conditions mentioned above, it is possible to purge the measurement of events that are far from the most probable measurements, consequently obtaining a more precise measurement. In any case, since these are signal definition processes known per se to those skilled in the art, they will not be further explored herein.

Experimentally, it has been found that events falling within the upper area represent ambient neutron events, while events falling within the lower area represent incident cosmic ray events.

It has also been experimentally noted that the measurement of the number of particles linked to incident cosmic rays is precise and in line with other methods of measurement of the cosmic ray flow.

According to possible alternative embodiments, the discrimination of ambient neutrons, incident cosmic rays and background/noise may be further improved by means of selections on more than three parameters of the same typology of the three parameters mentioned above.

The calculation of parameters similar to the first parameter and the third parameter may be done with different fractions (for example 25%, 50%, 66%, etc.). These parameters are all related to each other, in different ways depending on the particle (neutrons, muons or background noise) that interacted with the particle.

For example, according to a possible embodiment, the discrimination between ambient neutrons, incident cosmic rays and background/noise may take place on the basis of six parameters:

1) first parameter in which the fraction of its maximum value is equal to 80%;
2) second parameter;
3) third parameter with a first time interval and condition of taking into consideration a delimited area in the Cartesian plane parameter number 3) and parameter number 2);
4) third parameter with a second time interval and condition of taking into consideration a delimited area in the Cartesian plane parameter number 4) and parameter number 3);
5) third parameter with a third time interval and condition to consider a delimited area in the Cartesian plane parameter number 5) and parameter number 3); and
6) first parameter in which the fraction of the maximum value is equal to 100%.

However, it should be noted that the example just provided is given for explanatory and non-limiting purposes only with regard to any combinations of parameters (first parameter, second parameter and third parameter) which may be taken into consideration for the detection and discrimination of the signals mentioned above.

Figure 6:
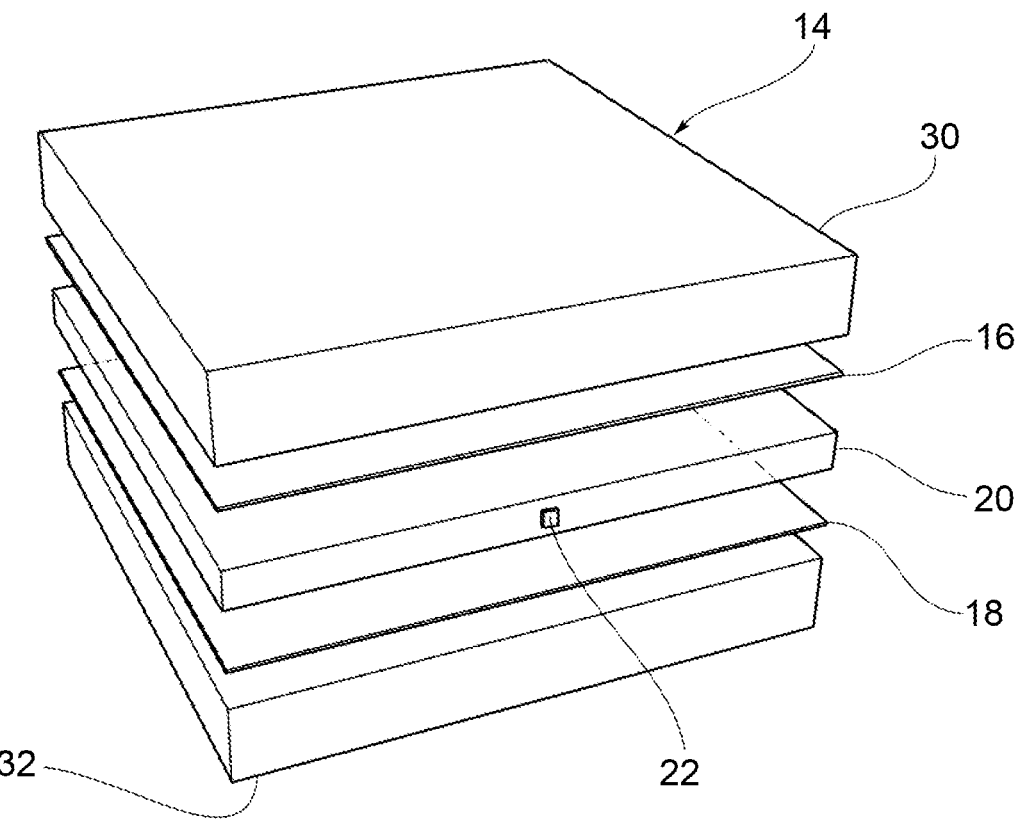
FIGS. 6 and 7 schematically show some components of a device according to two possible embodiments of the present invention, in partially exploded views.
Figure 7:
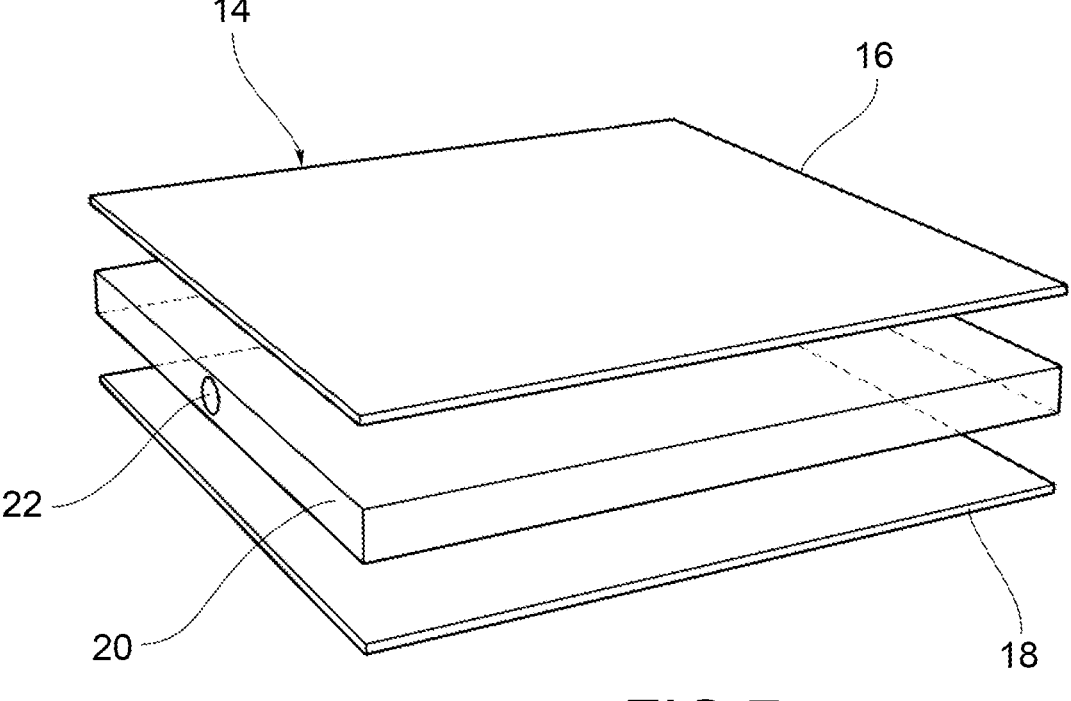

According to a possible embodiment of the present invention, the at least one ambient neutron detector 14 may comprise polyethylene coating sheets 30, 32, adapted to moderate the energy of the ambient neutrons. As shown in the example of FIG. 6, the coating sheets may be provided on the external surface of the first sheet 16 and of the second sheet 18.

The polyethylene of which the coating is composed may be high or low density, and may have a thickness ranging from 5 to 50 mm.

According to a possible embodiment, the first sheet 16 and the second sheet 18 comprise scintillator crystals in a silicone-based matrix.

Advantageously, the first sheet 16 and the second sheet 18 may comprise scintillator crystals and Lithium (for example enriched Li-6) or Boron-based (for example enriched B-10) crystals in a silicone-based matrix.

The silicone matrix ensures greater mechanical strength of the scintillator sheets and better heat resistance than other types of matrix.

According to a possible embodiment, the first sheet 16 and the second sheet 18 may comprise ZnS(Ag) scintillator crystals.

As known, the scintillator is a material capable of emitting pulses of light, in the visible or ultraviolet range, when it is crossed by high-energy photons or charged particles. Being a known material in itself, it will not be further described.

The light guide 20 may be made as a wavelength shifting (WLS) solid plate or as a WLS optical fiber bundle. By WLS is meant a material which, hit by a certain wavelength, emits one of a different wavelength.

The wavelength shift reduces the self-absorption effects in the emitting material and allows the scintillation light to be efficiently transported up to the light meter 22, 24.

Figures 4, 5:
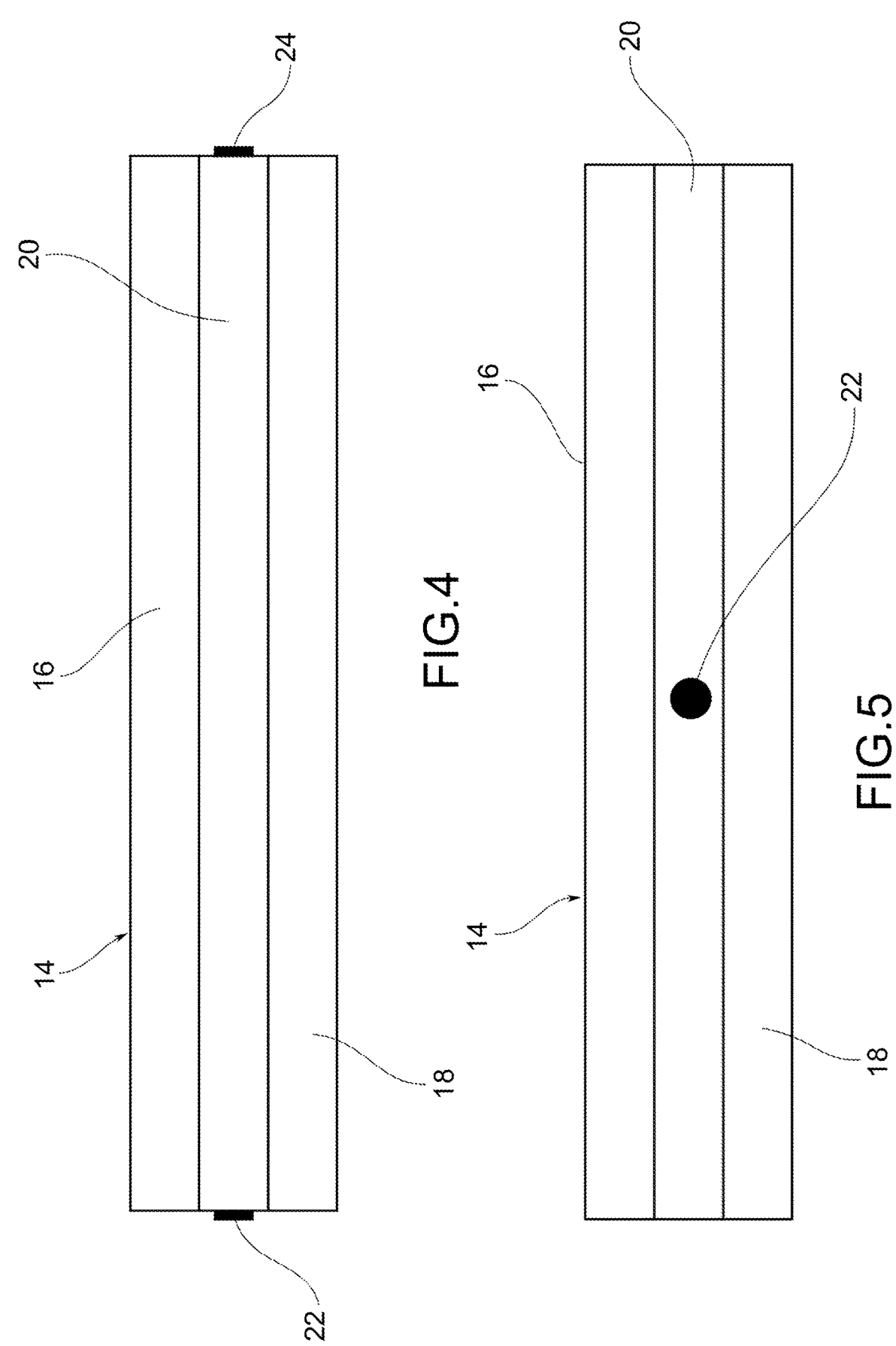
FIGS. 4 and 5 schematically show a lateral view and a front view of a component of a device according to the present invention.

Advantageously, the detector may comprise two or more light meters 22, 24, adapted to measure the light conveyed by the light guide 20. According to a possible embodiment, shown in the example of FIG. 4, the two light meters 22, 24 may be provided at two opposite sides of the light guide 20.

According to a possible embodiment, the at least one second module light meter 22, 24, adapted to measure the light conveyed by the light guide 20, may be a silicon photomultiplier (SiPM).

As is known, silicon photomultipliers are produced directly from a layered silicon structure on which matrices consisting of microcell arrays on a silicon substrate are arranged. Each microcell is a single photon avalanche photodiode (APD).

SiPM type photomultipliers have very low volumes, weight, consumption and prices compared to traditional photomultipliers with vacuum tubes. They are also extremely robust from a mechanical point of view and do not require a high voltage power supply (about 1000 V) typical of photomultiplier tubes.

The use of at least two SiPM read in coincidence allows the electronic noise of the SiPM to be drastically reduced even at low thresholds.

The first sheet 16 and the second sheet 18 may have a substantially square arrangement having a side length between 50 mm and 300 mm and a thickness between 0.2 mm and 1.0 mm.

Advantageously, the basic structure already described, consisting of a light guide 20 and two detector sheets 16 and 18, may be extended, in order to increase the detection efficiency and reduce the measurement times, by superimposing a second light guide above the sheet 16 followed by a third detector sheet; in the same way, further light guides may be added followed by further detector sheets, thus creating a multi-layer structure consisting of light guides type 20 alternating with detector sheets type 16, 18.

Advantageously, the ambient neutron detector 14 may comprise a plurality of sheets 16, 18, for example three, wherein a light guide 20 is provided between the two sheets.

According to a possible embodiment, the device may comprise an electric power supply (not shown) with at least one solar panel and a buffer battery.

Advantageously, the device may have dimensions equal to or less than a cube having a side of 500 mm.

Moreover, the device lends itself to being made water-proof, in particular it may be (IP66).

The control unit, in the modular logic of the device, may appear as a dedicated board containing a series of channels with standard components to discriminate and integrate the electrical signals produced by the SiPM, such as the integrating circuit 28.

The board may also provide low voltage SiPM power supply (a few tens of Volts) with a feedback system to compensate for deviations due to temperature variations.

Advantageously, the board may be adapted to be able to house the electronics necessary for several modules for measuring the ambient neutron flow.

The signals selected by the control units may be digitized and read by a low consumption Linux micro PC (Raspberry PI, Beaglebone or equivalent), which processes them in real time using dedicated pulse shape analysis software.

The device 12 may also be set up with a remote connection module (not shown) which allows the data processed to be sent externally, through a Wi-Fi connection or equivalent, or GSM, to an external server.

Advantageously, the formation, digitization and processing of signals, the management of power supplies and the sending of data processed externally may be achieved with a dedicated ultra-low power (<0.5 W) board, allowing to further reduce the size and the costs of the solar panel and the buffer battery, a particularly useful aspect for using the device in the open field.

According to a possible alternative embodiment, the discrimination of the neutrons, cosmic rays, background noise signals may be realized by means of properly trained neural networks or equivalent neural algorithms.

The method for measuring the water content of the ground, vegetation and/or snow, comprising the steps of:

providing a device 12 for measuring the water content of the ground, vegetation and/or snow of the type just described;

processing by the control unit 26 the signal generated by the integrating circuit so as to discriminate a signal generated by ambient neutron, cosmic rays and/or background noise, and obtaining a measurement of ambient neutron flow, cosmic rays, and/or background noise;

obtaining the measurement of the water content of the ground, vegetation and/or snow from the measurement of the normalized ambient neutron flow with respect to the measurement of the cosmic rays flow incident to the ground.

As mentioned above, the processing by the control unit 26 of the signal generated by the integrating circuit so as to discriminate a signal generated by ambient neutrons, cosmic rays and/or background noise, may be carried out by calculating at least three parameters wherein:

a first parameter is the time necessary for the signal to reach a predetermined fraction of its maximum value;

a second parameter is the maximum value of the signal;

a third parameter is the ratio between the partial charge in a time interval having a predetermined length and the total integrated charge.

Through the use of these parameters, the signals are distinguishable from each other on the basis of correlations between the types of parameters mentioned above.

The advantages that may be achieved with a device and a method according to the present invention are now apparent.

Firstly, a device is provided which is very compact and cost-effective compared to devices using similar technology currently available.

Furthermore, a device is provided which is easier to manage than the devices of the prior art, since it is provided with a single type of detector module.

Furthermore, the device is less complex and less expensive than known devices.

Furthermore, the smaller number of active components of the device results in greater robustness and reliability over time compared to known devices.

Furthermore, from experimental tests the device has proved to be more precise and reliable than known systems in measuring the water content.

Furthermore, the device is simpler to calibrate and manage, and is therefore more stable and reliable than the devices of the prior art.

The present device may be used for example for:

research in the hydrogeological/climatological field: measurement of the water content of the ground for the validation of forecast models with short and long term monitoring;

research in the snow/glaciological field: monitoring of the water content present in the nivoglacial basin; the data is interesting to monitor especially in spring to know the water availability and monitor any sudden floods caused by sudden melting of the snow.

climatological monitoring: long-term monitoring of local climatic variability.

precision irrigation: knowledge of the water content of the ground to optimize the moisture present in the ground in order to minimize the need for treatments or irrigation and maximize agricultural production.

Those skilled in the art will be able to make modifications to the embodiments described above or substitute described elements with equivalent elements, in order to satisfy particular requirements, without departing from the scope of the accompanying claims.

The invention claimed is:

1. A device for measuring water content of ground, vegetation and snow, comprising:

at least one ambient neutron detector adapted to measure an ambient neutron flow, the at least one ambient neutron detector comprising at least a first sheet and a second sheet made at least partially with a scintillator, a light guide interposed between said first and second sheets; said ambient neutron detector further comprising at least one light meter adapted to measure light conveyed by said light guide;

said at least one ambient neutron detector being adapted to transform interaction of the device with at least one particle into an electric charge;

said device further comprising a programmable control unit operatively connected to said at least one ambient neutron detector, wherein said programmable control unit comprises an integrating circuit in which the electric charge produced by the interaction with said at least one particle is transformed to a first signal;

said control unit being adapted to process said first signal to discriminate a second signal generated by ambient neutron flow, incident cosmic rays and/or background noise, and obtaining a measurement of ambient neutron flow, incident cosmic rays, and/or background noise;

wherein a measurement of the water content of the ground, vegetation and snow is obtained from a measurement of normalized ambient neutron flow with respect to a measurement of cosmic rays flow incident to the ground; and wherein said control unit is adapted to calculate at least three parameters wherein: a first parameter is time necessary for the first signal to reach a predetermined fraction of a maximum value; a second parameter is the maximum value of the first signal; and a third parameter is a ratio between a partial charge in a time interval having a predetermined length and a total integrated charge; said first and second signals being distinguishable between each other based on correlations between types of parameters.

2. The device according to claim 1, wherein discrimination of the neutrons, cosmic rays, background noise signals is realized by trained neural networks or equivalent neural algorithms.

3. The device according to claim 1, wherein said at least one ambient neutron detector comprises polyethylene coating sheets, adapted to moderate energy of ambient neutrons, said coating sheets being provided on an external surface of said first sheet and said second sheet.

4. The device according to claim 1, wherein said first sheet and said second sheet comprise scintillator crystals in a silicone-based matrix.

5. The device according to claim 1, wherein said first sheet and said second sheet comprise scintillator crystals and Lithium or Boron-based crystals in a silicone-based matrix.

6. The device according to claim 1, wherein said first sheet and said second sheet comprise ZnS(Ag) scintillator crystals.

7. The device according to claim 1, wherein said light guide is a WLS solid plate or a wavelength shifting (WLS) optical fiber bundle.

8. The device according to claim 1, wherein said at least one ambient neutron detector comprises two light meters adapted to measure light conveyed by said light guide.

9. The device according to claim 1, wherein said at least one light meter adapted to measure the light conveyed by said light guide is a silicon photomultiplier.

10. The device according to claim 1, wherein said ambient neutron detector comprises a plurality of sheets, comprising light guides between two of said plurality of sheets.

11. A method for measuring water content of ground, vegetation and/or snow, comprising the steps of:

providing a device for measuring the water content of the ground, vegetation and/or snow comprising at least one ambient neutron detector adapted to measure an ambient neutron flow, comprising at least a first sheet and a second sheet made at least partially with a scintillator; a light guide between said first sheet and said second sheet; said ambient neutron detector further comprising at least one light meter adapted to measure light conveyed by said light guide;

said ambient neutron detector being adapted to transform interaction of the device with at least one particle into an electric charge;

said device further comprising a programmable control unit and operatively connected to said at least one ambient neutron detector;

wherein said programmable control unit comprises an integrating circuit in which the electric charge produced with the interaction with said at least one particle is transformed to a first signal;

processing by the control unit the first signal generated by the integrating circuit to discriminate a second signal generated by ambient neutron, incident cosmic rays and/or background noise, and obtaining a measurement of ambient neutron flow, incident cosmic rays, and/or background noise;

obtaining a measurement of the water content of the ground, vegetation and/or snow from a measurement of normalized ambient neutron flow with respect to a measurement of cosmic rays flow incident to the ground;

wherein said control unit is adapted to calculate at least three parameters wherein: a first parameter is time necessary for the first signal to reach a predetermined fraction of a maximum value; a second parameter is the maximum value of the first signal; and a third parameter is a ratio between a partial charge in a time interval having a predetermined length and a total integrated charge; said first and second signals being distinguishable between each other based on correlations between types of parameters.

* * * * *